United States Patent [19]

Heymann

[11] Patent Number: 5,951,989
[45] Date of Patent: *Sep. 14, 1999

[54] METHOD FOR THE TREATMENT OF DRY SKIN

[76] Inventor: Warren R. Heymann, One Hundred Brick Rd., Suite 306, Marlton, N.J. 08053

[*] Notice: This patent issued on a continued prosecution application filed under 37 CFR 1.53(d), and is subject to the twenty year patent term provisions of 35 U.S.C. 154(a)(2).

[21] Appl. No.: 08/838,379

[22] Filed: Apr. 7, 1997

[51] Int. Cl.$^6$ ............................. A61K 6/00; A61K 38/00
[52] U.S. Cl. ........................ 424/401; 424/78.06; 514/5; 514/886; 514/887; 530/380
[58] Field of Search ..................... 424/401, 464, 424/70.15, 562, 568, 78.03, 78.06, 78.07; 512/5; 514/886, 887, 885, 889, 859, 861, 863, 864, 870; 530/388.72, 399, 380

[56] References Cited

U.S. PATENT DOCUMENTS 5,614,178  3/1997  Bloom et al. .............................. 424/60
5,631,248  5/1997  Davis et al. ............................. 514/179

OTHER PUBLICATIONS

Bukhanova et al, Local effect of hormonal factors on the course of repair processes in the skin of irradiated animals, Viniti 2667–78, 38–9 (Russian), 1978.

Velasco et al, Reticular erythematous Mucinosis and acral papulakeratotic lesions associated with myxoedema due to hashimoto thyroiditis, Dermatology, 184, 73–77, 1992.

Bukhonova, A.I. and Mirolyubova, Local Effect of Hormonal Factors on the Course of Repair Processes in the Skin of Irradiated Animals, Proceedings of a Conference of the OMSK Division of the All–Russian Scientific Society of Anatomy, Histology, and Embryology (1978).

Velaso, J. A., J. C., Villabona, V. and Santana, J. Reticular erythematous mucinosis and acral papulkeratotic leisons associated with myxoedema due to Hasimoto thyroiditis. Dermatology; 184:73–77, 1992.

*Primary Examiner*—Thurman K. Page
*Assistant Examiner*—L. Channavajjala
*Attorney, Agent, or Firm*—William J. McNichol, Jr.; R. Anthony Diehl

[57] ABSTRACT

A method for the treatment of dry skin by applying an effective amount of thyroid hormone in a pharmaceutically acceptable carrier to the skin.

6 Claims, No Drawings

METHOD FOR THE TREATMENT OF DRY SKIN

FIELD OF THE INVENTION

This invention relates to methods for the treatment of abnormally dry skin, a dermatologic disorder sometimes known as xerosis.

DESCRIPTION OF THE PRIOR ART

Dry skin of varying severity has long been recognized as a dermatologic disorder. The condition is associated with cracking, peeling, redness and sometimes bleeding in the affected areas. Patients find it very uncomfortable and esthetically undesirable. In severe cases it may progress beyond discomfort and unsightly appearance to more serious secondary conditions, including asteotic eczema with or without secondary infection.

Known methods of treating dry skin include the application of a variety of moisturizers such as lanolin, lanolin alcohol, mineral oil, dimethicone, lactic acid and ammonium lactate. These and other moisturizers, alone or in combination with one another are applied to abnormally dry skin to alleviate this condition. Most are effective to some degree, but none are entirely satisfactory.

Thyroid hormone, the well recognized product of the thyroid gland is also known as thyroxine, 3, 3', 5, 5' tetraiodothyronine or $T_4$. In circulation it is sometimes deiodinated to a more potent form, 3, 3' 5' triiodothyronine, or $T_3$.

The role of both the $T_4$ and $T_3$ forms of thyroid hormone in the regulation of metabolism is well known. Oral thyroid replacement therapy has become a standard treatment for hypothyroidism, the underproduction of thyroid hormone by the thyroid gland.

Myxedema is a peculiar form of dermal edema that has been recognized for over 100 years as characteristic of untreated hypothyroidism. Treatment of the underlying hypothyroidism with thyroid replacement therapy alleviates myxedema. See, Lund, P. et al., Acta Endocrinologica, Vol. 113, pp. 56–58 (1986).

Thyroid hormone is known to have some dermatologic side effects. In livestock, it has been shown to induce alopecia, an extensive loss of hair. See, Moore, P. G., et al., J. Invest. Dermatol. . Vol. 84, pp. 172–75 (1985). It has also been shown to influence tissue development and tissue differentiation in both the fetus and newborn. See, Housman, G. J., Pediatric Research, Vol. 2, pp. 204–11 (1992); North, D., et al., Pediatric Research, Vol. 31, pp. 330–34 (1992); Salido, E. C., Endocrinology, Vol. 127, pp. 2263–69 (1990); Watson, A. Y., et al., Endocrinology, Vol. 110. pp. 1392–1401 (1982). The action of thyroid hormone is generally described in Burgi, U. and Konig, M. P., Clin. Endo. and Metab., Vol. 2, pp. 567–89 (1988). While thyroid replacement therapy has been shown to be effective in the treatment of hypothyroidism, it has been reported to be ineffective in the treatment of nonthyroidal illnesses. See, Chopra, I. J., et al., J. Endocrinol. Invest., Vol. 10, pp. 559–64 (1987).

SUMMARY OF THE INVENTION

It has now been discovered that the topical application of thyroid hormone is an effective treatment for severe dry skin.

DETAILED DESCRIPTION OF THE INVENTION

According to the present invention, thyroid hormone in the form of $T_4$, $T_3$ or a mixture of them is mixed with a dermatologically acceptable vehicle and applied to clean skin which exhibits from xerosis.

The amount of thyroid hormone applied to the affected area will vary with the location of the affected area, the severity of the xerosis, and the overall condition of the skin in and around the affected area. The determination of the application rate and frequency of application of thyroid hormone in accordance with the present invention will also require the use of some clinical judgment based on patient chemistries and reactions, patient compliance and other factors that are necessarily left to the case-by-case clinical judgment of the treating physician. The amount of thyroid hormone used in the method of the present invention can also be affected by the ratio of the $T_4$ and $T_3$ forms in the thyroid hormone preparation. Because the $T_3$ form is significantly more potent than the $T_4$ form, a higher proportion of $T_3$ will result in the use of less thyroid hormone. In the experimental work described in this application, a thyroid preparation pure synthetic $T_4$ was used.

When applied to the face, application rates of from amount 0.100 to 0.001 $\mu g/cm^2$ of skin can be used. A typical high strength application is in the range of 0.035 to 0.045 $\mu g/cm^2$. A low strength application is about 0.004 to 0.008 $\mu g/cm^2$ and a mid-strength application rate is about 0.02 to 0.01 $\mu g/cm^2$. These application rates can be conveniently achieved using lotions having thyroid hormone concentrations of from about 0.5 to 10.0 $\mu g/ml$. The actual concentration of the thyroid hormone in the vehicle will be varied to achieve the desired application rate. The concentration of thyroid hormone may also be varied to account for the physical properties of the lotion, gel or cream used as a carrier. The thyroid hormone containing lotion is preferably applied twice a day.

A lotion suitable for use in connection with this invention was prepared as follows: Two hundred micrograms of lyophilized thyroxine was solubilized in a gel vehicle. This was further diluted with additional gel vehicle to a total volume of 30 cc. The resulting product had the following composition.

TABLE I

| Ingredient | % | in 30 cc |
|---|---|---|
| Levothyroxine (lyophilized) | 0.00067% w/v | 200 mcg. |
| Butylated Hydroxyanisole | 0.15% w/v | 0.045 gm |
| Disodium EDTA as 10% aqueous solution | 0.15% w/v | 0.045 gm |
| Dimethylisosorbide | 0.50% w/v | 0.150 gm |
| Laureth-4 | 1.00% w/v | 0.300 gm |
| Glycerin | 2.00% w/v | 0.600 gm |
| Propylene Glycol | 2.00% w/v | 0.600 gm |
| Ethanol, 200 proof | 36.80% w/v | 11.58 cc |
| Distilled Water, sufficient to make 100.00% | | |

Butylated Hydrosyanisole is an antioxidant that acts as a preservative. EDTA is a chelating preservative. Dimethylisosorbide, glycerin, propylene glycol and ethanol are used to enhance penetration. Water serves as a solvent and carrier. The affected area should be cleansed before the thyroid hormone lotion is applied. The lotion may be applied with a cotton swab, cotton ball of soft cloth and allowed to dry in place.

Five patients suffering from xerosis were treated in accordance with the present invention at an application rate of about 0.0167 $\mu g/cm^2$. All were free of thyroid disorders and had normal levels of thyroid hormone. Table II reports the results of their treatment. The initial condition of each patient is reported as a score on a 0–4 scale and shows that all patients suffered from moderate to severe xerosis. One patient also suffered from erythema (reported on the 0–4 scale). After three weeks of treatment, xerosis was significantly reduced in two patients and eliminated in two others. The remaining patient showed no change. Erythema was significantly reduced in the one patient that presented this condition. Thyroid hormone levels in each patient remained unchanged at the end of the treatment.

Additionally, each patient's pulse rate and blood pressure was essentially unchanged. This same treatment was also applied to a comparison group of five volunteers who did not suffer from either xerosis or the thyroid disorders. At the conclusion of the treatment, there were no dermatologic changes or effects in any member of the comparison group, nor were there any changes in blood pressure, pulse rate or thyroid hormone levels.

TABLE II

| Patient age/gender | Before Treatment | | | After Treatment | | |
|---|---|---|---|---|---|---|
| | Xerosis | Erythema | $T_4$* | Xerosis | Erythema | $T_4$* |
| 80 F | 3 | — | 11.3 | 3 | — | 11.3 |
| 50 F | 3 | — | 11.9 | 0 | — | 10.8 |
| 48 F | 4 | — | 6.1 | 0 | — | 6.3 |
| 47 F | 4 | 3 | 6.9 | 2 | 2 | 6.9 |
| 71 F | 3 | — | 6.8 | 2 | — | 6.3 |

*Micrograms/deciliter

From this data it can be seen that the topical application of thyroid hormone dramatically reduces xerosis and associated erythema. This treatment is effective in healthy patients with normal thyroid function and does not adversely affect the patient's thyroid hormone balance or induce effects attributable to hyper-thyroidism.

The foregoing is provided by way of non-limiting example. The scope of this invention is defined only by the following claims.

I claim:

1. A method for the treatment of dry skin comprising applying an amount of thyroid hormone effective to treat dry skin in a pharmaceutically acceptable carrier to the skin of a person in need of such treatment.

2. The method of claim 1, wherein the thyroid hormone is synthetic $T_4$.

3. The method of claim 1, wherein the concentration of thyroid hormone in the carrier is from about 0.25 to about 10.0 µg/ml.

4. The method of claim 1, wherein from about 0.001 to about 0.10 µg of the thyroid hormone is applied to each square centimeter of dry skin.

5. The method of claim 1, wherein from about 0.01 to about 0.02 µg of thyroid hormone is applied to each square centimeter of dry skin.

6. The method of claim 1, wherein the carrier comprises butylated hydroxyanisole, disodium EDTA, dimethylisosorbide, laureth-4, glycerin, propylene glycol, and ethanol.

* * * * *